0-631 SR
25/85 XR RE 31,924

United States Patent [19]

Starr, deceased

[11] E Patent Number: Re. 31,924

[45] **Reissued Date of Patent:* Jun. 25, 1985**

[54] COMPOSITION AND METHOD FOR STIMULATION OF BACTERIA

[75] Inventor: Jerry Starr, deceased, late of Holtville, Calif., by Walter C. Williams, administrator

[73] Assignee: Biohumus, Inc., Holtville, Calif.

[ * ] Notice: The portion of the term of this patent subsequent to Jan. 20, 1998 has been disclaimed.

[21] Appl. No.: 592,393

[22] Filed: Mar. 21, 1984

Related U.S. Patent Documents

Reissue of:

[64] Patent No.: 4,321,142
Issued: Mar. 23, 1982
Appl. No.: 184,401
Filed: Sep. 15, 1980

U.S. Applications:

[63] Continuation-in-part of Ser. No. 86,934, Oct. 22, 1979, Pat. No. 4,246,100.

[51] Int. Cl.[3] ..... C02F 3/00

[52] U.S. Cl. ..... 210/610; 210/631; 210/916; 252/180

[58] Field of Search ..... 210/609, 610, 611, 620, 210/631, 916, 749; 252/180

[56] References Cited

U.S. PATENT DOCUMENTS

| | | | |
|---|---|---|---|
| 3,227,648 | 1/1966 | Hahn et al. | 210/610 |
| 3,361,555 | 1/1968 | Herschler | 210/611 |
| 3,362,905 | 1/1968 | Gleave | 210/610 |
| 3,558,434 | 1/1971 | Herschler | 210/620 |
| 3,855,121 | 12/1974 | Gough | 210/610 |
| 4,119,429 | 10/1978 | Lovness | 71/6 |
| 4,246,100 | 1/1981 | Starr | 210/749 |

FOREIGN PATENT DOCUMENTS

| | | | |
|---|---|---|---|
| 52-12766 | 1/1977 | Japan | 210/609 |

*Primary Examiner*—Benoit Castel
*Attorney, Agent, or Firm*—Brown, Martin & Haller

[57] ABSTRACT

Composition for stimulation of [aerobic] bacteria in sewage or in soil from combination of B vitamins and an agent derived from digestion of milch cow excrement; and method of treating sewage or soil to stimulate the growth of [aerobic] bacteria to improve the condition of sewage for disposal or availability of soil nutrients for plant growth by addition of the composition to sewage or soil.

7 Claims, No Drawings

COMPOSITION AND METHOD FOR STIMULATION OF BACTERIA

Matter enclosed in heavy brackets [ ] appears in the original patent but forms no part of this reissue specification; matter printed in italics indicates the additions made by reissue.

This application is a C-I-P of Ser. No. 86,934, 10-22-79, now U.S. Pat. No. 4,246,100.

BACKGROUND OF THE INVENTION

This invention relates to the treatment of sewage or soil to improve its condition and to a composition for use in that treatment.

In my co-pending application, Ser. No. 86,934, filed Oct. 22, 1979, now U.S. Pat. No. 4,246,100 entitled "Composition and Method for the Treatment of Sewage", of which the present application is a continuation-in-part, it is disclosed that the combination of triacontanol and an organic soil treating agent derived from milking shed wastes reduces sludge and development of noxious odors when mixed with sewage. That application also indicates that the action of the triacontanol is improved by addition of B vitamins. The composition is very effective and provides long lasting action. However, at present, the material, triacontanol, is in limited supply and expensive.

BRIEF STATEMENT OF THE INVENTION

The composition of the present invention provides a less expensive, but useful, combination of an organic soil treating agent derived from milking shed wastes in which [aerobic] bacteria-stimulating action is obtained through coaction of that agent with B vitamins. Addition of this combination product to sewage in accordance with the present method reduces the development of noxious odors and improves the condition of the sewage for disposal. Also, it has been found that when applied to soil, the composition substantially increases the rate of plant growth over that from the application of the soil treating agent alone.

DETAILED DESCRIPTION

I have now found that growth of [aerobic] organisms in sewage or soil is greatly stimulated by a treating agent composed of a proprietary soil treating agent in combination with B vitamins. The combination of these materials, without the expensive material triacontanol, is useful for the treating of sewage containing animal or human excrement to reduce sludge, minimize the development of noxious odors and to facilitate disposal of residual components by percolation or otherwise. Additionally, when the composition is applied to soil, it stimulates [the aerobic] organisms in the soil so that plants can more effectively use nutrients in the soil.

The proprietary material for combination with vitamin B components is sold as "Biohumus" and is described as an almost water white, thin liquid product obtained by a first digestion of milch cow excrement with yeast under mildly acid conditions and at least one further digestion of the liquid separated from the first digestion products by the action of algae and solar radiation.

For combination with the liquid digestion products to provide the new sewage or soil treating agent, only small amounts of the B vitamins, thiamine, riboflavin and niacin are required. Percentages as low as from 0.02% to about 0.15% by weight of each of these vitamins components based on the weight of the treating agent have been found satisfactory and there does not appear to be any upper limit.

The combination of the liquid digestion product with these very small amounts of the B vitamin components to give unexpectedly strong growth stimulation of [aerobic] organisms in sewage or soil is believed to show a special interaction between these materials. That is, the liquid digestion product and the B vitamins have no significant bacteria content, and the amount of B vitamin relative to the volume of sewage or soil treated is negligible. Accordingly, it would appear that some continuing association is established between the B vitamins and the liquid digestion product when they are brought together since the combination provides a continuing ability to stimulate [aerobic] organisms in sewage or soil to which the combination has been added.

For treatment of sewage, the treating agent is simply mixed with the sewage and allowed to act. Treatment of large volumes of sewage, e.g., washings from a milking shed, may involve feeding the treating agent into a stream of the washings at a controlled rate to mix the treating agent with the washing and discharging the mixture into a disposal pond. Supply of the treating agent is cut off when the amount introduced into the disposal pond is sufficient to give the desired results, after which supply of the washings to the pond is continued. The introduction of further washings stirs up the pond and provides further liquids which, it is believed, are useful in maintaining the activity of the treating agent.

Effective sludge reducing action is obtained where as little as 40 ppm. of the combination product are added and a preferred range of addition is from about 40 to about 4000 ppm. of the treating agent based on the weight of the sewage to be treated.

Application of the treating agent to soil may be effected by adding the agent to the irrigation or sprinkler water supplied to a field. Addition of as little as about ten gallons of the treating agent to the water supplied to an acre has been found to give significantly better uniformity and rate of plant growth and to contribute to plant health as indicated by the color of the foliage.

The following examples are given to aid in understanding the invention, but it is to be understood that the invention is not limited to the particular procedures, conditions or materials of the examples.

EXAMPLE 1

Treating agent according to the present invention was prepared by mixing a 12.5 mg. of thiamin, 6.25 mg. of riboflavin, 12.5 mg. of niacin and 125 mg. of magnesium chloride with 17.7 ml. of the liquid product of digestion of milch cow excrement with yeast under mild acid conditions and further digestion of liquid portions by the action of algae and solar radiation ("Biohumus", a proprietary product of Biohumus, Inc. of Holtville, Calfornia).

A second treating agent according to the invention of my co-pending application identified above was prepared by mixing 17.7 ml. of the digestion product (Biohumus), 0.025 mg. of triacontanol, 12.5 mg. of thiamin, 6.25 mg. of riboflavin, 12.5 mg. of niacin and 125 mg. of magnesium chloride.

A first sample was prepared comprising five pounds of wet manure from a diary milking shed to which the treating agent of the invention was added and this material was disposed in a white translucent pail and mixed with tap water to a volume of 4½ gallons.

A second sample was prepared in which the second treating agent was added, disposed in a white translucent pail and mixed with tap water to a volume of 4½ gallons.

The pails containing the samples were set under a skylight for exposure to sunlight which approximated 50% of summer daylight.

Bacteria counts made on the samples are recorded in the following table:

| | Initial | 10th Day | 23rd Day |
|---|---|---|---|
| Sample #1 | | | |
| Standard Plate Count, 32° C., per ml. | 320,000 | 15,000,000 | 130,000,000 |
| Sample #2 | | | |
| Standard Plate Count, 32° C., per ml. | 310,000 | 20,000,000 | 140,000,000 |

The above results show that the combination of the liquid digestion product and B vitamins according to the present invention was nearly as effective in increasing the development of [aerobic] bacteria as was the combination of the liquid digestion product, triacontanol and B vitamins of the co-pending application.

EXAMPLE 2

A further batch of treating agent of the present invention was prepared as in Example 1. This treating agent was mixed with irrigation water and supplied to a portion of a field at the rate of ten gallons of treating agent for each acre of that portion of the field. Lettuce was then planted in the treated portion.

The digestion product (Biohumus) alone was supplied to a further portion of the field by addition to the irrigating water at the rate of ten gallons per acre and this portion of the field was also planted with lettuce.

As the plants grew in the field, it was observed that the lettuce in the portion of the field treated with the composition of the present invention was substantially larger and more uniform than the lettuce grown in the portion of the field treated with the digestion product alone. Also, the lettuce in the field treated with the agent of the present invention had distinctly better foliage color than the lettuce in the other portion of the field.

Having described my invention, what I claim is:

1. A composition for addition to sewage or soil to stimulate the growth of [aerobic] bacteria comprising the product of combining (1) the liquid product of a first digestion of milch cow excrement under mild acid conditions and further digestion of liquid portions from the first digestion by the action of algae and solar radiation, (2) at least 0.02% by weight of each of thiamine, riboflavin and niacin based on the weight of said liquid digestion product to activate a [n aerobic] bacteria-stimulating action and (3) at least 0.4% by weight of magnesium chloride.

2. A composition as defined in claim 1 in which said composition comprises from 0.02% to about 0.15% by weight of each of thiamine, riboflavin and niacin based on the weight of said liquid digestion product.

3. A method for the treatment [for sewage to stimulate the growth of aerobic bacteria] *of sewage to stimulate the growth of bacteria* comprising mixing with said sewage at least about 40 ppm. based on the weight of said sewage of a treating agent comprising the product of combining (1) the liquid product of a first digestion of milch cow excrement with yeast under mild acid conditions and further digestion of liquid portions from the first digestion by the action of algae and solar radiation, (2) at least 0.02% by weight of each of thiamine, riboflavin and niacin based on the weight of said liquid digestion product *to activate bacteria-stimulating action* [to activate [aerobic] bacteria-stimulating action] and (3) at least 0.4% by weight of magnesium chloride.

4. A method for the treatment of sewage as defined in claim 3, wherein the resultant mixture is exposed to sunlight.

5. A method for the treatment of sewage as defined in claim 4, in which said digestion product is combined with from about 0.02% to about 0.15% by weight of each of thiamine, riboflavin and niacin based on the weight of said digestion product.

6. A method for the treatment of soil [to stimulate the growth of aerobic bacteria] *to stimulate the growth of bacteria* comprising applying to the soil at least about 10 gallons per acre of soil of a treating agent comprising the product of combining (1) the liquid product of a first digestion of milch cow excrement with yeast under mild acid conditions and further digestion of liquid portions from the first digestion by the action of algae and solar radiation, (2) at least 0.02% by weight of each of thiamine, riboflavin and niacin based on the weight of said liquid digestion product to activate [aerobic] bacteria-stimulating action and (3) at least 0.4% by weight of magnesium chloride.

7. A method for the treatment of soil as defined in claim 6, in which said digestion product is combined with from about 0.02% to about 0.15% by weight of each of thiamin, riboflavin and niacin based on the weight of said digestion product.

* * * * *